United States Patent

Kansal et al.

(10) Patent No.: US 6,846,952 B2
(45) Date of Patent: Jan. 25, 2005

(54) PROCESS FOR MANUFACTURE OF A 4-BROMO-2-OXYIMINO BUTYRIC ACID AND ITS DERIVATIVES

(75) Inventors: Vinod Kumar Kansal, Mandideep (IN); Dnyandeo Ragho Rane, Mandideep (IN); Sanjay Deshmukh, Mandideep (IN); Santosh Kumar Singh, Mandideep (IN); Santosh Richaria, Mandideep (IN); Susan Ajay Abraham, Mandideep (IN)

(73) Assignee: Lupin Limited (IN)

( * ) Notice: Subject to any disclaimer, the term of this patent is extended or adjusted under 35 U.S.C. 154(b) by 0 days.

(21) Appl. No.: 10/465,926

(22) PCT Filed: Jun. 7, 2002

(86) PCT No.: PCT/IN02/00130

§ 371 (c)(1),
(2), (4) Date: Jun. 26, 2003

(87) PCT Pub. No.: WO03/045899

PCT Pub. Date: Jun. 5, 2003

(65) Prior Publication Data

US 2004/0054224 A1 Mar. 18, 2004

(30) Foreign Application Priority Data

Nov. 26, 2001 (IN) ................................. 1124/MUM/2001

(51) Int. Cl.$^7$ ............................................... C07B 39/00
(52) U.S. Cl. ....................... 562/603; 562/553; 562/574; 562/602
(58) Field of Search ................ 562/512, 553, 562/602, 603

(56) References Cited

U.S. PATENT DOCUMENTS 5,095,149 A * 3/1992 Tani et al. .................. 562/560

FOREIGN PATENT DOCUMENTS

| EP | 0 030 294 B1 | 11/1980 | ......... C07D/501/36 |
|---|---|---|---|
| EP | 0 246 603 B1 | 5/1987 | ......... C07C/249/00 |
| EP | 0 324 418 A2 | 1/1989 | ........... C07C/69/72 |
| EP | 0 325 183 A2 | 7/1989 | ......... C07C/131/00 |
| EP | 0 416 857 B1 | 1/1995 | ......... C07C/251/60 |
| GB | 2 012 276 A | 7/1979 | ......... C07D/501/20 |

* cited by examiner

Primary Examiner—Johann Richter
Assistant Examiner—Karl Puttlitz
(74) Attorney, Agent, or Firm—Pendorf & Cutliff

(57) ABSTRACT

A process for producing 4-bromo-2-oxyimino butyric acid, predominantly as the (Z)-isomer of formula (I),

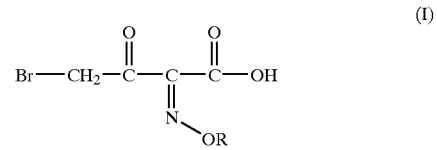

(I)

wherein R is hydrogen; a linear or branched $C_{1-4}$ alkyl group; a linear or branched $C_{1-4}$ alkyl group substituted by a carboxylic acid or an aryl group; a substituted or unsubstituted cyclic alkyl group of 3–6 carbon atoms or a substituted or unsubstituted aryl group. The product is produced by reacting bromine with a 2-(oxyimino)-3-oxo butyric acid derivative of formula (II)

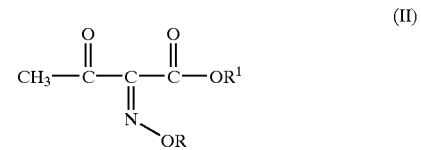

(II)

wherein R is as defined above and $R^1$ is a tert-butyl group in presence of an organic solvent and in presence of a $C_{1-4}$ alcohol and acetyl bromide at a temperature ranging from about −15° C. to about +15° C. Bromine is used in a proportion of about 0.90 to about 1.35 moles per mole of compound (II), preferably 0.90 to 1.10 moles. The acetyl bromide is used in molar proportions of 0.9 to 2 moles per mole of compound (II), preferably 0.9 to 1.5 moles.

12 Claims, No Drawings

PROCESS FOR MANUFACTURE OF A 4-BROMO-2-OXYIMINO BUTYRIC ACID AND ITS DERIVATIVES

CROSS REFERENCE TO RELATED APPLICATION

This application is a national stage of PCT/IN02/00130 filed Jun. 07, 2002 and is based upon Indian Application No. 1124/MUM/2001, filed Nov. 26, 2001 under the International Convention.

FIELD OF THE INVENTION

The present invention relates to an efficient large scale synthesis of 4-bromo-2-oxyimino butyric acid, predominantly as the (Z)-isomer of formula (I) in high purity and substantially free of any di-or polybromo derivatives and other impurities. The compounds of formula (I) are valuable as intermediates for synthesis of commercially important cephalosporin antibiotics containing a 2-(2-aminothiazol-4-yl)-2-(substituted)oxyimino acetic acid moiety attached to the 7-amino position.

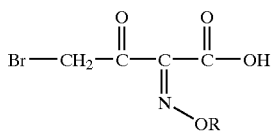

BACKGROUND OF THE INVENTION

The 4-bromo-2-oxyimino butyric acid and its derivatives of formula (I), wherein R is hydrogen or a protective group are generally prepared by two methods, both starting from diketene of formula (IV)

Method 1: By step-wise bromination of the 2-oxyimino-3-oxo butyric acid derivatives of formula (II),

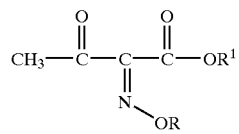

wherein R is as defined above and $R^1$ together with the carboxylic acid group (—COO) to which it is attached forms a carboxylic acid ester group and hydrolysis of the ester group $R^1$ or simultaneous bromination and hydrolysis in one step.

The compounds of formula (II) in turn are obtained by oxyimination of acetoacetic acid esters of formula (III, in turn obtained by reaction of diketene (IV) with an alcohol), wherein $R^1$ is as defined above by reaction with sodium nitrite in the presence an acid to give the oxyiminated product (II), wherein R is hydrogen. The oxyiminated compound of formula (II), wherein R is hydrogen on alkylation with appropriate alkylating agents gives the substituted oxyiminated derivatives of formula (II), wherein R is a protective group.

Scheme-I

Method-1

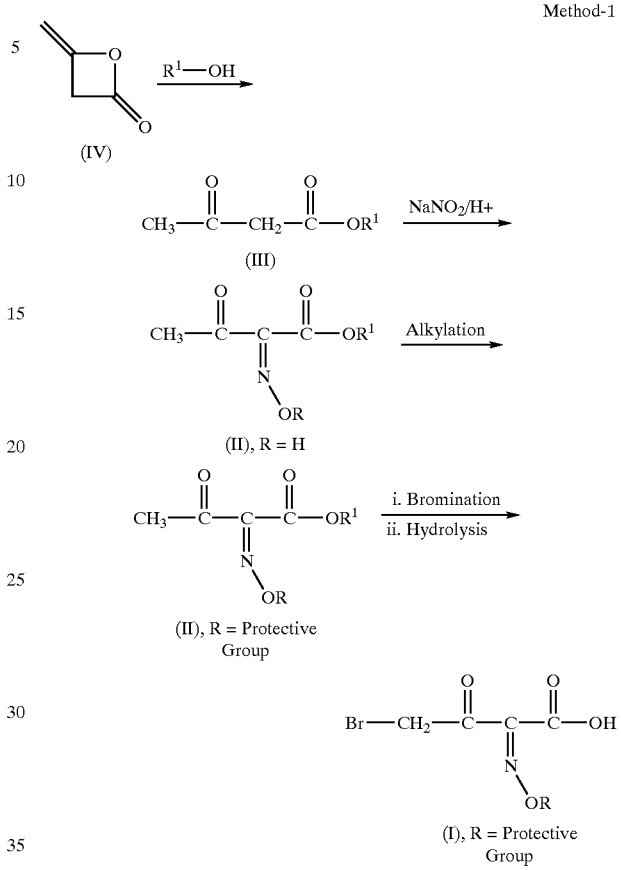

Method-2

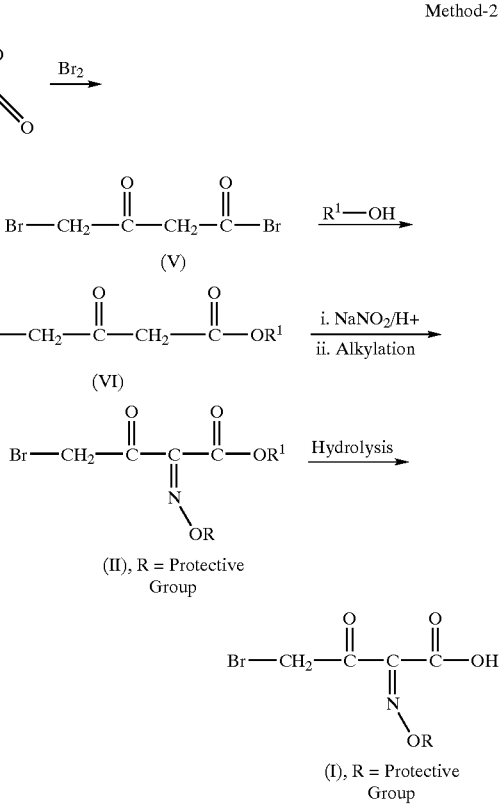

Method 2: Bromination of diketene of formula (IV) to give the dibromo derivative (V), which on reaction with an alcohol $R^1$—OH gives the bromoester of formula (VI), which on further oxyimination with sodium nitrite in the presence of an acid gives the oxyiminated product of formula (II), wherein R is hydrogen. As mentioned hereinabove, the oxyiminated compounds of formula (II), wherein R is hydrogen on alkylation with appropriate alkylating agents give the substituted oxyiminated derivatives of formula (II), wherein R is a protective group.

The chemistry employed in the two general methods is summarised in Scheme-I.

Commercially, the compounds of formula (I) are manufactured by Method-1, since many of the acetoacetic acid ester derivatives of formula (III) are readily available. Method-2, on the other hand has limited application and is restricted to those manufacturers who in turn produce diketene. Moreover, the dibromo derivatives (V) being unstable cannot be stored and are therefore, not available commercially.

The prior art methods whereby compound of formula (I) is produced by Method-1 are summarised hereinbelow:

i) EP Patent No. 0 030 294 (Montavon et. al.) describes preparation of compound (I), wherein R is methyl from compound (II), wherein R has the same meaning as defined above and $R^1$ is a tert-butyl group comprising first hydrolysis of the tert-butyl ester group with trifluoroacetic acid to give the corresponding free carboxylic acid derivative, which is brominated with about 0.72 moles of bromine per mole of the hydrolysed derivative in a mixture of dichloromethane and methanol to give the crude brominated compound (I), which is crystallised from carbon tetrachloride in an overall yield of 36%.

The shortcomings of the method are that it involves a) two step process of hydrolysis and halogenation, b) use of large excess (about 12 molar excess, thereby increasing the cost of manufacture) of the toxic and corrosive trifluoroacetic acid for hydrolysis the excess amount of which is removed by distillation thereby subjecting the unstable oxymino butyric acid to heat, c) formation of di- and polybromo derivatives and other impurities during bromination affecting the quality of the product and d) which necessiates purification taking recourse to crystallisation of the impure material from carbon tetrachloride, a highly toxic and suspected carcinogenic solvent.

A similar method is described in GB Patent No. 2 012 276 whereby compound of formula (I) is obtained first by hydrolysis of the group $R^1$ (methyl or ethyl) in compound (II) using alkali, followed by halogenation of the free carboxylic acid derivative thus obtained.

ii) The alkaline hydrolysis, however, proceeds in low yields, implying formation of considerable amounts of impurities.

iii) The method described in EP Patent Nos. 0 324 418 and 0 325 183 (Naito et. al.) comprise hydrolysis of the group $R^1$ (tert-butyl) of tert-butyl-2-methoxyimino-3-oxo butyrate by bubbling dry hydrogen chloride gas into a solution of the oxyimino ester in an anhydrous organic solvent selected from halogenated hydrocarbons, tetrahydrofuran and dioxane. The hydrolysed free carboxylic acid derivative thus obtained is brominated using bromine in presence of dichloromethane and a solution of hydrogen bromide in acetic acid. The brominated compound (I, R=methyl) after purification is obtained in an overall yield of only 11.60% from the starting ester compound.

In addition to involving a two-step process and proceeding in overall low yields the hydrolysis step is very slow and takes about 13–23 hours for completion. Moreover, the method utilises hazardous tetrahydrofuran and the industrially not accepted dioxane for hydrolysis.

iv) In the method disclosed in EP Patent No. 0 246 603 (Tani et. al.) a 2-oxyimino-3-oxo-butyric acid ester is reacted with a silylating agent to produce the corresponding 3-silyloxy derivative, which is halogenated at the 4-position. Hydrolysis of the ester protective group gives compounds of formula (I).

However, the shortcomings of the method are, a) an additional step of silylation, adding to the cost of manufacture, b) utilisation of very low temperature (Ca. −30° C.) for halogenation and c) purification of the halogenated derivative by chromatography, not practical on industrial scale.

v) Tani et. al. in EP Patent No. 0 416 857 claim a one-pot and one-step synthesis of compounds of formula (I) by subjecting the tert-butyl ester of compound (II) to bromination in an etherial solvent or a mixture of ether and inert solvent selected from carbon tetrachloride, toluene and benzene. Two molar equivalents of bromine per mole of the ester is employed. The final compound (I) is obtained in a yield of 42–46%.

The major disadvantage of the method is the use of ether solvents, which are prone to explosion and use of toxic and carcinogenic carbon tetrachloride and benzene.

To summarise, the methods described in the prior art for synthesis of 4-bromo-2-oxyimino butyric acid (I) from the ester derivative (II) suffer from one or more of the following shortcomings. These are, viz.

a) separate steps for hydrolysis of the ester group $R^1$ and bromination at the 4-position, b) use of toxic, corrosive and costly chemicals like trifluoroacetic acid for hydrolysis, c) utilisation of tetrahydrofuran and etherial solvents, which are prone to explosion and utilisation of environmentally benign solvents such as benzene, carbon tetrachloride and dioxane for the hydrolysis, bromination and purification/crystallisation steps, d) use of bromine in up to two molar equivalents of the starting ester, leading to formation of considerable amounts of di- and poly-brominated derivatives and other impurities, e) necessity of removing the impurities by crystallisation from a solvent or mixture of solvents or through chromatography, f) shortcomings a) to e) leading to overall low yield, increase in time and cost of manufacture and environmentally benign processes for manufacture of compounds of formula (I) and g) finally, shortcoming f) in turn, leading to lower conversions and lower yields when compounds of formula (I) are utilised as intermediates for synthesis of commercially important cephalosporin antibiotics carrying a 2-(2-aminothiazol-4-yl)-2-oxyimino acetic acid group attached to the 7-amino position of the β-lactam nucleus.

OBJECT OF THE INVENTION

It is thus the basic object of the invention to provide a process for manufacture of 4-bromo-2-oxyimino-3-oxo butyric acid, predominantly as the (Z)-isomer of formula (I) which would avoid the aforediscussed shortcomings/problems associated with the prior art methods discussed above.

Another object of the present invention is to provide a one-step and one-pot process for manufacture of compound of formula (I) which would be convenient, safe and cost-effective.

Yet another object of the present invention is directed to provide a process for manufacture of compound of formula (I) which would be substantially free of impurities.

Yet further object of the present invention is to provide an effecient process for manufacture of 7-[2-(2-aminothiazol-4-yl)-2-oxyimino acetamido]-3-cephem compounds in high yield and purity by utilisation of compound of formula (I).

SUMMARY OF THE INVENTION

Thus, according to the present invention there is provided a one-pot and one-step process for producing 4-bromo-2-oxyimino butyric acid predominantly as the (Z)-isomer of formula (I) in high purity and substantially free of any di-or polybromo derivatives and other impurities,

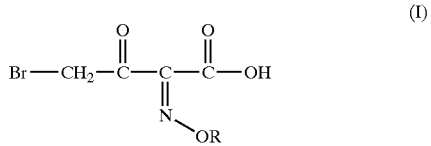

(I)

wherein R is hydrogen; a linear or branched $C_{1-4}$ alkyl group; a linear or branched $C_{1-4}$ alkyl group substituted by a carboxylic acid or an aryl group; a substituted or unsubstituted cyclic alkyl group of 3–6 carbon atoms or a substituted or unsubstituted aryl group which comprises reacting a 2-oxyimino-3-oxo butyric acid derivative of formula (II)

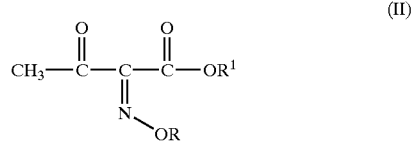

(II)

wherein R is as defined above and $R^1$ is a tert-butyl group with bromine in presence of an organic solvent and in presence of acetyl bromide and a $C_{1-4}$ alcohol at a temperature ranging from about –15° C. to about +15° C., thereby effecting simultaneous cleavage of the ester linkage and bromination of the methyl group at 4-position.

DETAILED DESCRIPTION OF THE INVENTION

The bromination of symmetrical and unsymmetrical ketones at the alpha($\alpha$)-position in an organic solvent is normally associated with formation of di- and poly-brominated products in addition to the desired mono-bromo derivative. It has been suggested [M. Gaudrey and A. Marcuer, *Organic Synthesis*, Coll. Vol. VI, pp 193–195] that formation of large amounts of di-brominated products when bromination of such symmetrical and unsymmetrical ketones is carried out in solvents selected from ether and carbon tetrachloride can be minimised on utilisation of methanol as solvent.

In our pending Indian Application, IN 83/MUM/2000 an improved method for bromination of β-keto iminoether acetoacetates was disclosed wherein one-step and one-pot bromination and hydrolysis of such β-keto iminoether acetoacetates of formula (II) to give compounds of formula (I) was carried out in a chlorinated hydrocarbon (dichloromethane) solvent in the presence of an alcoholic solvent. The utilisation of an alcoholic solvent, specially methanol resulted not only in formation of lesser amounts of the di-and poly-brominated products, but also in the reduction of the quantity of bromine required for the reaction. The said bromination and hydrolysis could be effectively carried out using 1.30 to 1.35 molar equivalents of bromine per mole of compounds of formula (II) as against the use of about 2.0 molar equivalents of bromine reported in the prior art, giving the mono-brominated compounds of formula (I) containing reduced amounts of di- and poly-brominated compounds as impurities. An intrinsic aspect of the method is that the reaction be initiated at a temperature of about 40 to 45° C.

It has been now surprisingly found that the two-steps of bromination and hydrolysis of compounds of formula (II) can be carried out in an organic solvent in presence of a $C_{1-4}$ alcohol and in the presence of acetyl bromide at lower temperatures, using substantially reduced quantities of bromine and without the need for initiation of the reaction at higher temperatures leading to an overall reduction in the formation of impurities and thereby giving the object mono-brominated compounds of formula (I) predominantly as the (Z)-isomer in higher yield and higher purity.

The present invention, therefore, relates to an improved method for manufacture of 4-bromo-2-oxyimino butyric acid of formula (I), wherein R is as defined hereinearlier, the improvement comprising reacting a 2-oxyimino-3-oxo butyric acid derivative of formula (II), wherein $R^1$ is a tert-butyl group with bromine in the presence of acetyl bromide in the presence of an organic solvent mixed with a $C_{1-4}$ alcohol. The use of acetyl bromide in conjuction with liquid bromine and a $C_{1-4}$ alcohol ensures that lower amounts of bromine, that is in a proportion of 0.90 to 1.35 molar equivalents per mole of compound of formula (II) is sufficient for complete bromination of the methyl group at 4-position and complete hydrolysis of the tert-butyl group, $R^1$ to give compounds of formula (I) in high purity, substantially free of any di- or poly-brominated derivatives and other impurities.

The method of the present invention, summarised in Scheme-II can be carried out in the following ways.

Scheme-II:
Process of the present invention

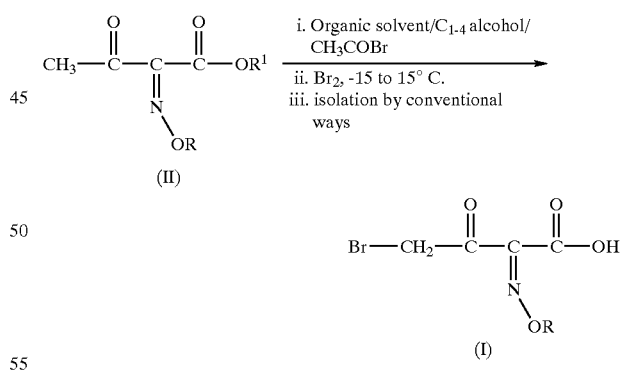

To a solution of tert-butyl 2-oxyimino-3-oxo butyrate of formula (II), wherein R is as defined herein earlier in an organic solvent mixed with a $C_{1-4}$ alcohol and acetyl bromide cooled to about –15° C. to about +15° C. is added a solution of liquid bromine in the same organic solvent slowly at the same temperature. After complete addition of the bromine solution, the reaction is agitated at about –15° C. to about +15° C. till completion of reaction. Work-up of the reaction is the conventional way, followed by evaporation and crystallization of the organic layer gives compounds of formula (I) in a purity >95%.

Alternatively, a solution of tert-butyl 2-oxyimino-3-oxo butyrate of formula (II), wherein R is as defined herein earlier in an organic solvent and acetyl bromide cooled to about −15° C. to about +15° C. is added a solution of liquid bromine in the same organic solvent mixed with a $C_{1-4}$ alcohol slowly at the same temperature. After complete addition of the bromine solution, the reaction is agitated at about −15° C. to about +15° C. till completion of reaction. Work-up of the reaction is the standard way, followed by evaporation of the organic solvent followed by the crystallization gives compounds of formula (I) in a purity >95%.

Both the variations in the method give the object compounds (I) in about the same yield and purity.

The organic solvents that can be used for carrying out the bromination reaction include among others chlorinated hydrocarbons such as dichloromethane and dichloroethane; esters of acetic acid such as methyl acetate, ethyl acetate and iso-propyl acetate as well as ether solvents such as diethyl ether and diisopropyl ether. Sufficient amount of solvent to keep the reaction mixture in solution is employed. Normally, about two to five times (by volume) of the solvent per amount (by weight) of the starting compounds of formula (II) is employed in the process. Among the solvents, chlorinated hydrocarbons and esters of acetic acid are preferred and among these dichloromethane and ethyl acetate are more preferred.

The $C_{1-4}$ alcohols can be used in molar proportions of about 1 to 8 moles per mole of the starting compounds of formula (II). Preferably, the alcohols are employed in molar proportions of about 1 to 2 moles per mole of the starting compounds of formula (II). The alcohols that can be employed in the method are selected from any $C_{1-4}$ alcohol, excepting tert-butanol. The alcoholic solvents that can be employed include methanol, ethanol, n-propanol, iso-propanol, n-butanol and iso-butanol. Amongst these methanol, ethanol are the most preferred.

Acetyl bromide used in the method can be employed in molar proportions of 1 to 2 moles per mole of compounds of formula (II) used, preferably in molar proportions of 1 to 1.5 moles. Commercially available acetyl bromide can be used as such without any purification in the process.

The reaction does not require any initiation and can be conveniently carried out by addition of bromine to a solution of compounds of formula (II) in any of the solvent mentioned hereinabove mixed with any of the alcohol mentioned hereinearlier and acetyl bromide at a temperature ranging from about −15° C. to about +15° C. A preferred range of temperature is from about −10° C. to about +5° C. The preferred temperature range is maintained throughout till completion of the reaction as monitored by HPLC.

Bromine in a molar proportion of about 0.90 to 1.35 moles per mole of compounds of formula (II) can be safely employed in the process without giving rise to formation of considerable amounts of impurities, specially the di- and poly-bromo derivatives. Preferably, a molar proportion of bromine from about 0.90 to 1.10 moles is employed to achieve higher conversion of the mono-brominated compounds of formula (I).

At the end of the reaction the organic solvent containing the brominated compounds of formula (I) is washed successively with an aqueous solution of sodium bisulfite or sodium dithionite, followed with water. The aqueous phase is separated from the organic phase after adjusting the pH to about near neutral. Acidification of the separated aqueous phase, extraction with an organic solvent, followed by evaporation of the organic solvent and crystallization with xylene or carbontetrachloride gives the desired Z isomer of compounds of formula (I) as an off-white solid in purity >95%.

The acid chloride of pure isomer thus obtained on reaction with 7-amino-3-substituted cephalosporin derivatives to give the 7-[4-bromo-2-oxyimino-3-oxo butanamido]-3-cephem compounds which on subsequent reaction with thiourea. furnished the pure z-isomer of 7-[2-(2-aminothiazol-4-yl)-2-oxyimino acetamido]-3-cephem compounds thus avoid the unnecessary purification of costly desired product.

The embodiments of the present invention can be best described by the following non-limiting examples.

EXAMPLE-1

Preparation of 4-bromo-2-methoxyimino-3-oxo Butanoic Acid:

tert-butyl 2-methoxyimino-3-oxo butyrate (120 gm, 0.597moles), acetyl bromide (72.50 gm; 0.5894 moles; 0.987 molar eq.) and methanol (55 gm; 1.77 moles; 2.97 molar eq.) were mixed in ethyl acetate (300 ml) at 5–10° C. To the solution thus obtained cooled to −6 to −10° C. was added dropwise a solution of bromine (96 gm; 0.600 moles; 1 molar eq.) in ethyl acetate (60 ml). The mixture was agitated at the same temperature till completion of reaction, after which it was washed with an aqueous solution of sodium dithionate, followed by saturated brine solution. The organic layer is separated and basified to adjust the pH between 6.50 to 7.00. The aqueous phase is separated and mixed with dichloromethane. The pH of the mixture is adjusted to 0.40 by addition of Conc. HCl. The organic layer is separated, washed with saturated brine solution and evaporated off under reduced pressure to give crude 110 gm (80.91%) of the title compound(Z:E=93:7) as viscous liquid.

Crystallization of crude bromo acid with carbontetrachloride yielded the Z-isomer (78 .0 g, 58%)

Similarly the crystallization of the same with Xylene or o-xylene afforded the pure Z isomer (82 g, 61%).

m. p: 75–78° C.;

IR (KBr): 1728, 1703, 1595, 1047 $cm^{-1}$ $^1$H NMR (200 MHz, $CDCl_3$): δ 3.85 (s, 3H, O$\underline{CH}_3$); 4.30 (s, 2H, Br—$\underline{CH}_2$)

$^{13}$C NMR (200 MHz, $D_2O$): δ 30.80 (C-4); 64.60 (N—OMe); 148.90 ($\underline{C}$=N); 163.80 ($\underline{C}$—OH); 188.50 ($\underline{C}$=O)

EXAMPLE-2

Preparation of 4-bromo-2-methoxyimino-3-oxo Butanoic Acid:

tert-butyl 2-methoxyimino-3-oxo butyrate (100 gm; 0.497 moles), acetyl bromide (60 gm; 0.488 moles; 0.98 molar eq.) and methanol (58 gm; 1.81 moles; 3.64 molar eq.) were mixed in dichloromethane (200 ml) at −5 to −10° C. To the solution thus obtained cooled to −12 to −10° C. was added dropwise a solution of bromine (78 gm, 0.488 moles; 0.98 molar eq.) in dichloromethane (100 ml). The mixture was agitated at the same temperature till completion of reaction, after which it was washed with an aqueous solution of sodium dithionate, followed by saturated brine solution. The organic layer is separated and basified to adjust the pH between 6.50 to 7.00. The aqueous phase is separated and mixed with dichloromethane. The pH of the mixture is adjusted to 0.40 by addition of Conc. HCl. The organic layer is separated, washed with saturated brine solution and evaporated off under reduced pressure to give crude 97 gm (85.720%) of the title compound (Z:E: 91:9) as viscous oil. The crystallization of the same either with carbontetrachloride, xylene or o-xylene yielded the pure Z-isomer.

EXAMPLE-3

Preparation of 4-bromo-2-methoxyimino-3-oxo Butanoic Acid:

tert-butyl 2-methoxyimino-3-oxo butyrate (50 gm, 0.248moles), acetyl bromide (31 gm; 0.25 moles; 1.0 molar eq.) and ethanol (23 gm; 0.5 moles; 2.0 molar eq.) were mixed in ethyl acetate (200 ml) at 5–10° C. To the solution thus obtained cooled to –6 to –10° C. was added dropwise a solution of bromine (39.68 gm; 0.248moles; 1 molar eq.) in ethyl acetate (50 ml). The mixture was agitated at the same temperature till completion of reaction, after which it was washed with an aqueous solution of sodium dithionate, followed by saturated brine solution. The organic layer is separated and basified to adjust the pH between 6.50 to 7.00. The aqueous phase is separated and mixed with dichloromethane. The pH of the mixture is adjusted to 0.40 by addition of Conc. HCl. The organic layer is separated, washed with saturated brine solution and evaporated off under reduced pressure to give crude 43 gm of the title compound(Z:E=90:10) as viscous liquid. The crystallization of the same with Xylene or o-xylene afforded the white crystalline solid, pure Z isomer (purity >97%, 30 g, 54%).

What is claimed is:

1. A process for producing 4-bromo-2-oxyimino butyric acid, predominantly as the (Z)-isomer of formula (I),

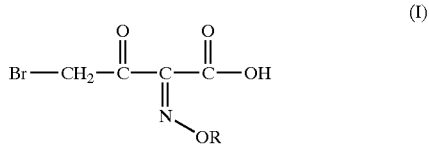

(I)

wherein R is is selected from the group consisting of hydrogen; a linear or branched $C_{1-4}$ alkyl group; a linear or branched $C_{1-4}$ alkyl group substituted by a carboxylic acid or an aryl group; a substituted or unsubstituted cyclic alkyl group of 3–6 carbon atoms and a substituted or unsubstituted aryl group which comprises reacting bromine with a 2-(oxyimino)-3-oxo butyric acid derivative of formula (II)

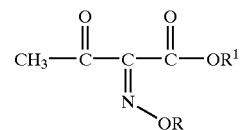

(II)

wherein R is as defined above and $R^1$ is a tert-butyl group in presence of an organic solvent and in presence of a $C_{1-4}$ alcohol and acetyl bromide at a temperature ranging from about –15° C. to about +15° C.

2. A process as claimed in claim 1 wherein the bromine is used in a proportion of about 0.90 to about 1.35 moles per mole of compound (II).

3. A process as claimed in claim 1 wherein the organic solvent is selected from the group consisting of dichloromethane, dichloroethane, methyl acetate, ethyl acetate, iso-propyl acetate, diethyl ether and diisopropyl ether with dichloromethane and ethyl/methyl acetate.

4. A process as claimed in claim 1 wherein the $C_{1-4}$ alcohol is selected from the group consisting of methanol, ethanol, n-propanol, iso-propanol, n-butanol and iso-butanol.

5. A process as claimed in claim 4 wherein the $C_{1-4}$ alcohol is selected from the group consisting of methanol, ethanol and propanol.

6. A process as claimed in claim 1, wherein the $C_{1-4}$ alcohol is used in a molar proportion of 1 to 8 moles per mole of compound (II).

7. A process as claimed in claim 1 wherein acetyl bromide is used in molar proportions of 0.9 to 2 moles per mole of compound (II).

8. A process as claimed in claim 1 wherein the reaction is carried out at a temperature from about –10° C. to about +5° C.

9. A process as claimed in claim 1 wherein the bromine is used in a proportion of about 0.90 to about 1.10 moles per mole of compound (II).

10. A process as claimed in claim 1 wherein the $C_{1-4}$ alcohol is used in a molar proportion of 1 to 3 moles per mole of compound (II).

11. A process as claimed in claim 1 wherein acetyl bromide is used in molar proportions of 0.9 to 1.5 moles per mole of compound (II).

12. A process as claimed in claim 1 wherein the organic solvent is selected from dichloromethane and ethyl/methyl acetate.

* * * * *